United States Patent [19]

Buckle et al.

[11] 4,405,620
[45] Sep. 20, 1983

[54] PIPERAZINE DERIVATIVES

[75] Inventors: Derek R. Buckle, Redhill; Harry Smith, Maplehurst Nr. Horsham, both of England

[73] Assignee: Beecham Group Limited, England

[21] Appl. No.: 227,621

[22] Filed: Jan. 19, 1981

[30] Foreign Application Priority Data

Jan. 19, 1980 [GB] United Kingdom ............... 8001856
Jul. 25, 1980 [GB] United Kingdom ............... 8024454

[51] Int. Cl.³ ................ C07D 413/00; A61K 31/495
[52] U.S. Cl. ................................... 424/250; 544/368; 544/366; 548/256; 548/259
[58] Field of Search ................. 544/368, 366; 424/250

[56] References Cited

FOREIGN PATENT DOCUMENTS 1454247 4/1973 United Kingdom .

OTHER PUBLICATIONS

Weilheimer, W., "Synthetic Methods of Organic Chemistry", vol. 15, p. 28, (1961).
Burton et al., "Comprehensive Org. Chem., The Synthesis and Reactions of Org. Cpds.", vol. 5, p. 354.
McOmie, J. F., "Protectine Groups in Org. Chem.", p. 198, (1973).
Marsh, et al., J. Org. Chem., 30, 2491 (1965).
Hoover et al., J. Amer. Chem. Soc., 1956, vol. 78, p. 5832-5836.
Wiley et al., J. Org. Chem., 1956, vol. 21, p. 190-192.
Albert, A. D., J. Chem. Soc. Perkin Trans. I, 1978, p. 513-516.
Dorgan et al., J. Chem. Soc. Perkin Trans I, 1980, p. 930, 940.
Chemical Abstracts, Tsuij, T. et al. 89:6100s.
Tetrahedron Letters vol. 21, p. 3731, 1980 Willard et al.
Tetrahedun Letters, vol. 16, p. 1327, 1970 Feutrill et al.

*Primary Examiner*—Nicholas S. Rizzo
*Assistant Examiner*—S. A. Gibson
*Attorney, Agent, or Firm*—Jacobs & Jacobs

[57] ABSTRACT

Compounds of the formula (I), or pharmaceutically acceptable salts thereof

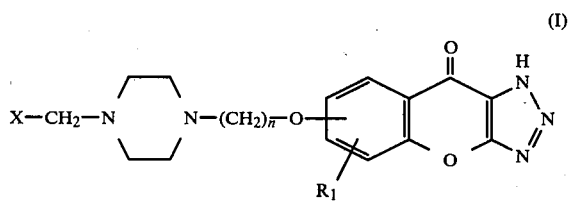

wherein X is phenyl, optionally substituted by one halogen, $C_{1-4}$ alkyl or $C_{1-4}$ alkoxy; or pyridyl; $R_1$ is hydrogen or $C_{1-6}$ alkyl; and n is 1 to 6, pharmaceutical compositions containing them and a process for their preparation. These compounds are useful in the prophylaxis or treatment of diseases due to a histamine-mediated allergic response.

9 Claims, No Drawings

PIPERAZINE DERIVATIVES

This invention relates to a novel class of compounds, their formulation into pharmaceutical compositions, and their use in therapy.

It is known that some types of cells are activated by certain antibody-antigen combinations and release substances which mediate the allergic response. British Patent Specification No. 1454247 discloses that certain substituted 3-nitrocoumarins have useful activity in that they appear to inhibit the release of substances such as histamine which are normally released after antibody-antigen combinations and which mediate the allergic response.

We have now discovered a class of compounds which not only inhibit the release of mediator substances but also antagonize the effects of histamine released after the above mentioned antibody-antigen combinations. Thus these compounds are of value in the prophylaxis or treatment of diseases whose symptoms are controlled by the mediators of the allergic response, for example asthma, hay-fever, rhinitis and allergic eczema.

Accordingly, the present invention provides a compound of the formula (I), or pharmaceutically acceptable salt thereof:

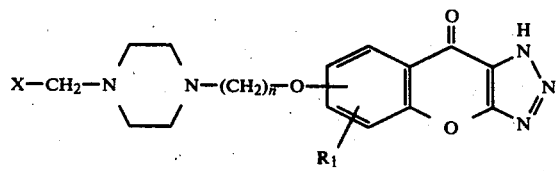
(I)

wherein X is phenyl, optionally substituted by one halogen, $C_{1-4}$ alkyl or $C_{1-4}$ alkoxy; or pyridyl; $R_1$ is hydrogen or $C_{1-6}$ alkyl; and n is 1 to 6.

When X is an optionally substituted phenyl group, then it may be represented:

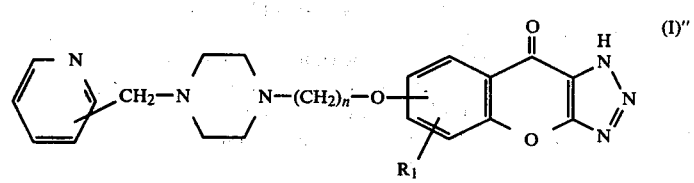

wherein R is hydrogen, halogen, $C_{1-4}$ alkyl or $C_{1-4}$ alkoxy. Suitable examples of R include hydrogen, fluorine, chlorine, bromine, methyl, ethyl, methoxy and ethoxy. More suitably R is hydrogen or halogen, preferably chlorine. Preferably R when halogen is in the o- or p-position and most preferably is p-chloro.

Alternatively X may be pyridyl. In such cases X is suitably 2- or 4-pyridyl, preferably 2-pyridyl.

Suitable examples of $R_1$ include hydrogen, methyl, ethyl and n- and iso-propyl. When other than hydrogen, $R_1$ is suitably in the 5-position (that is, substituting the carbon atom adjacent the oxygen atom joined bridgehead carbon atom). Preferably $R_1$ is hydrogen or 5-methyl.

n is suitably 2, 3 or 4, preferably 3.

The side chain oxygen atom may join the benzopyrano[2,3-d]-v-triazole nucleus at any non-bridgehead carbon in the benzo moeity. Suitably however it will be joined at the 6-position (that is, substituting the carbon atom meta- to the oxygen atom joined bridgehead carbon atom).

Within formula (I) there is a group of compounds of formula (I)':

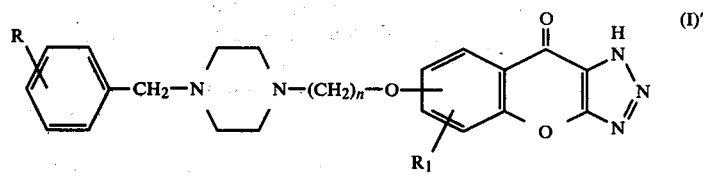
(I)' wherein R is hydrogen, halogen, $C_{1-4}$ alkyl or $C_{1-4}$ alkoxy; $R_1$ is hydrogen or $C_{1-6}$ alkyl; and n is 1 to 6.

Suitable and preferred examples of the variable groups therein are as described in relation to formula (I).

Within formula (I) there is also a group of compounds of formula (I)":

(I)"

wherein $R_1$ is hydrogen or $C_{1-6}$ alkyl; and n is 1 to 6.

Suitable and preferred examples of the variable groups therein are as described in relation to formula (I).

From the aforesaid it will be appreciated, that one preferred sub-group of compounds of the formula (I) is of formula (II):

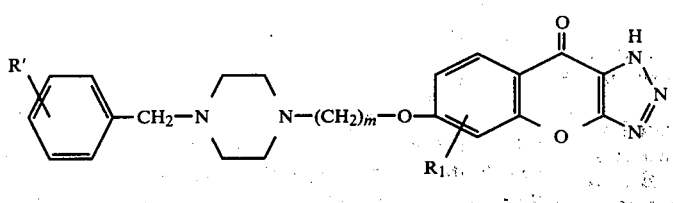

wherein R' is hydrogen or halogen, $R_1$ is hydrogen or $C_{1-6}$ alkyl, and m is 2, 3 or 4.

Suitable and preferred values for R', $R_1$ and m are as hereinbefore described for R, $R_1$ and n respectively.

Thus R' when halogen is preferably in the o- or p-position, most preferably p-chloro.

Similarly $R_1$ when alkyl is preferably in the 5-position, preferably hydrogen or 5-methyl.

The triazole moiety of the compounds of formula (I) has an acidic hydrogen, and accordingly may form salts. Examples of pharmaceutically acceptable salts falling within the scope of this invention include the aluminium, alkali metal and alkaline earth metal salts such as the sodium, potassium and magnesium salts; and salts with ammonia, organic bases and amino compounds. The compounds of the formula (I) may also form salts of the amino moieties, such as salts with hydrochloric and sulphuric acid.

The present invention also provides a process for the preparation of a compound of the formula (I), or a pharmaceutically acceptable salt thereof which process comprises the de-protection of a compound of the formula (III).

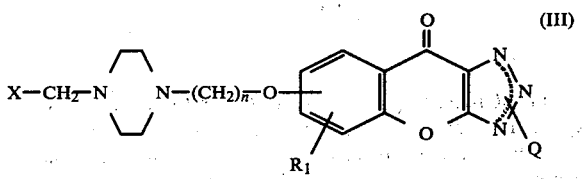

wherein $Q^1$ is a protecting group and the other variables are as defined in formula (I); and optionally thereafter salifying the compound of the formula (I) so obtained.

Suitable examples of $Q^1$ groups are N-protecting groups such as labile benzyl groups, for example $C_{1-6}$ alkoxy substituted benzyl groups. One particularly suitable example of $Q^1$ is 4-methoxybenzyl.

The protecting group $Q^1$ may be removed in any convenient way which does not disrupt any other part of the molecule. For example we have found that acid catalysis is generally suitable. It is preferable to use the p-methoxybenzyl protecting group which is readily removed using trifluoroacetic acid, the course of the cleavage being followed by high pressure liquid chromatography or by NMR spectroscopy. Suitably temperatures of around 50°-70° C. can be used, with a suitable reaction time being around 2-10 hours. Other strong acids such as methanesulphonic acid behave similarly.

The compounds of the formula (III) may themselves be prepared by coupling a compound of the formula (IV) with a compound of formula (V):

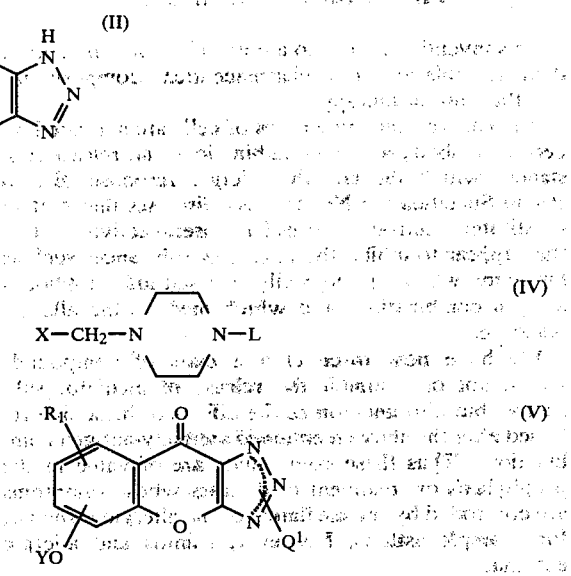

wherein L is hydrogen and Y is a group $Z(CH_2)_n$ where Z is a group readily displaceable by a nucleophile from an aliphatic moiety; or L is a group $(CH_2)_nOH$ and Y is hydrogen; and n is as defined in formula (I).

When L is hydrogen and Y is a group $Z(CH_2)_n$, suitable examples of Z include halogen atoms such as chlorine, bromine and iodine, and activated ester groups such as methanesulphonate and tosylate groups.

The reaction is generally carried out in the presence of a moderate base in a polar solvent. Examples of suitable bases include basic alkali metal salts such as the carbonates, for instance potassium carbonate. Examples of suitable solvents include ketones; such as methyl ethyl ketone.

The reaction is conveniently carried out under reflux at temperatures of 50° to 110° C. depending on the solvent, base and particular starting materials employed. The reaction time will depend on these parameters and on the temperature employed and this may readily be determined by routine trial and error. The reaction may be monitored by conventional methods such as thin layer chromatography. By way of example a reaction time of up to 6 hours is often suitable.

Compounds of formula (IV) in this case are either known compounds or may be prepared analogously to known compounds.

Compounds of the formula (V) wherein Y is $Z(CH_2)_n$ as hereinbefore defined may be prepared by the reaction of a corresponding compound of the formula (V) wherein Y is H, with a compound of the formula (VI):

A(CH$_2$)$_n$B     (VI)

wherein A is Z as hereinbefore defined or hydroxyl and B is chlorine, bromine or iodine, and, when A is hydroxyl, subsequently esterifying A to give an activated ester group.

The reaction is generally carried out in the presence of the bases and solvents and at the temperatures described as suitable for the reaction of compounds of formulae (IV) and (V).

When, in the compounds of formulae (IV) and (V), L is a group $(CH_2)_nOH$ and Y is hydrogen, the reaction is these compounds is generally carried out in the presence of a compound of formula (IX):

wherein $R_3$ and $R_4$ are independently $C_{1-6}$ alkyl, aryl or aryl-$C_{1-6}$ alkyl, generally both ethyl, and a compound of formula (X):

wherein $R_5$, $R_6$ and $R_7$ are independently $C_{1-6}$ alkyl, $C_{1-6}$ alkoxy, aryl, aryloxy, aryl-$C_{1-6}$ alkyl or aryl-$C_{1-6}$ alkoxy, generally all phenyl.

The reaction is generally carried out at a nonextreme temperature, such as $-20°$ to $100°$ C., in an inert aprotic organic solvent such as tetrahydrofuran, dioxan, ethyl acetate or benzene.

The compounds of formula (V) wherein Y is hydrogen may be prepared in three ways.

Firstly, a compound of formula (XI) may be protected:

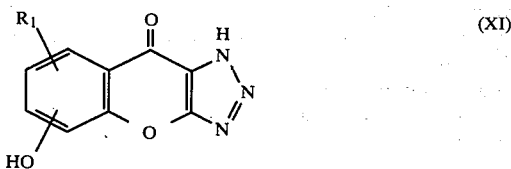

for example by reaction with $Q^1B$ as defined, under conventional conditions, e.g. as described for the reaction of compounds of formula (IV) and (V).

Secondly, a compound of formula (XII)

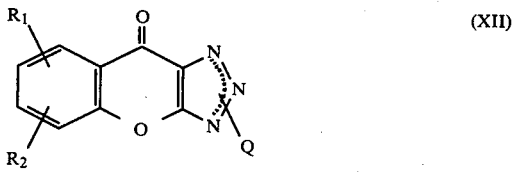

wherein $R_2$ is $C_{1-4}$ alkylsulphonyloxy, such as methylsulphonyloxy, or p-toluenesulphonyloxy, and Q is hydrogen or an N-protecting group $Q^1$ as hereinbefore defined, may be hydrolysed to give a compound of the formula (XI) or (V) (Y=H) respectively; a compound of the formula (XI) so obtained may be protected as described hereinbefore to give a compound of the formula (V) where Y=H.

This hydrolysis is suitably carried out under akaline conditions.

Thirdly, compounds of the formula (V) (Y=H) may be prepared by the dealkylation of a compound of the formula (XIII):

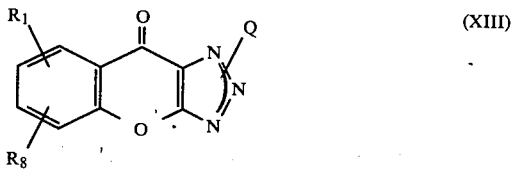

wherein Q is hydrogen or an N-protecting group, $R_8$ is $C_{1-4}$ alkoxy and $R_1$ is hydrogen or $C_{1-6}$ alkyl; and thereafter if necessary converting Q when an N-protecting group to hydrogen.

Dealkylation may suitably be effected with lithium iodide in 2,4,6-collidine by the method of Harrison, Chem. Commum, 1969, 616 in which a solution of the ether in dry collidine containing a modest excess of lithium iodide is refluxed for up to 24 hours under an inert atmosphere such as nitrogen.

It may also suitably be effected with borontrihalidedimethylsulphide complexes by the method of Williard et al., Tetrahedron Letters, 1980, 3731, in which a two to four-fold excess of the complex in 1,2-dichloroethane is refluxed with the ether for up to 30 hours under an inert atmosphere such as nitrogen.

Suitable reaction conditions for the conversion of Q are as described for compounds of formula (III).

Demethylation may suitably be effected with a base such as sodium thioethoxide in a polar solvent such as dimethylformamide, at moderately elevated temperatures, such as $130°$ to $170°$ C., following the procedure of Feutrill et al., Tet. Letters, 1970, 1327. Reflux for 24 hr. in dimethylformamide is usually sufficient for reaction.

Cyclisation of a compound of formula (XIV) yields the hereinbefore defined compounds of formula (XII):

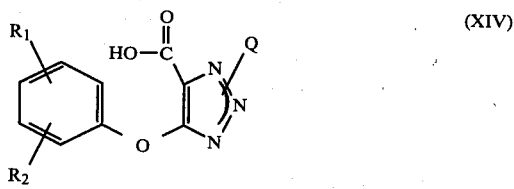

The cyclisation is preferably carried out in the presence of polyphosphoric acid or phosphorus pentoxide and methane sulphonic acid.

Compounds of the formula (XIII) may be prepared by the cyclisation of a compound of the formula (XV):

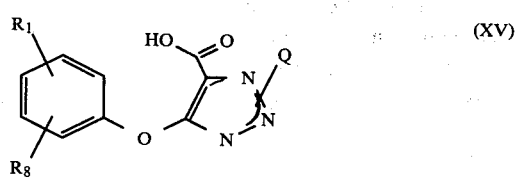

wherein Q, $R_1$ and $R_8$ are as defined in formula (XIII).

The cyclisation is suitably effected under the same conditions as that of the compound of the formula (XIV).

Alternatively, when Q is an N-protecting group, the compound of the formula (XV) may be converted to its acid chloride (for example by treatment with thionyl chloride and cyclisation of the acid chloride effected under Friedel-Crafts conditions, e.g. in dichloromethane, optionally under reflux, in the presence of aluminium trichloride.

Intermediates of the formulae (XIV) and (XV) may be represented by a common formula (XVI):

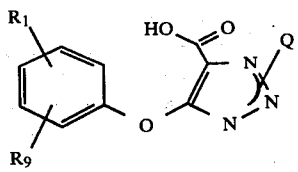

(XVI)

wherein $R_9$ is $R_2$ or $R_8$ as defined in formulae (XII) and (XIII).

When the phenyl group of the compound of formula (XVI) is non-symmetric about the ring-O bond, and the 2- and 6- positions with respect to the triazolyloxy side chain taken as 1 are unsubstituted then a mixture of two isomers results from cyclisation. These may be separated conventionally for example by fractional crystallisation or column chromatography.

The cyclisation is best carried out at elevated temperature i.e. above 40° C. but less than 120° C. We have found temperatures between 50° and 105° C. to be convenient.

Compounds of formula (XVI) wherein $R_9$ is $R_2$, i.e. of formula (XIV) may be prepared by sulphonation of the corresponding compound of formula (XVII):

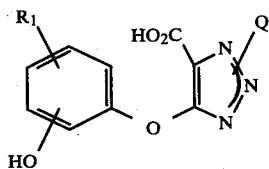

(XVII)

This sulphonation is carried out in conventional manner.

It should be noted that when mesylation is desired, this may suitably be carried out with a solution of phosphoric oxide in anhydrous methane-sulphonic acid, and if the reaction temperature is held at about 95° C. this mesylate gradually cyclises to the corresponding compound of formula (XII) as defined above.

The compound of formula (XIV) may alternatively be prepared by sulphonation of an ester of formula (XVIII):

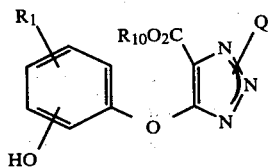

(XVIII)

wherein $R_{10}$ is $C_{1-6}$ alkyl, such as ethyl; or benzyl; and subsequent de-esterification.

Analogous etherification may be used for compounds of the formula (XV) but Q must then be an N-protecting group in the compound of formula (XVIII) which may be converted subsequently to hydrogen if desired.

The compound of formula (XVIII) is suitably prepared by hydrogenation of a compound of formula (XIX):

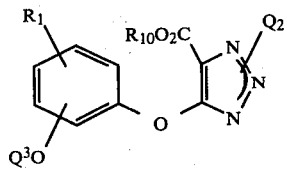

(XIX)

wherein $Q^2$ is a hydrogenolysable N-protecting group; and $Q^3$ is a hydrogenolysable O-protecting group to give a compound of formula (XVIII) as defined above, and subsequent de-esterification (with for example sodium hydroxide).

Suitable groups $Q^2$ and $Q^3$ include benzyl, 4-methylbenzyl and 4-nitrobenzyl and $Q^1$ as hereinbefore defined.

The aforesaid hydrogenation is conveniently carried out under conditions which remove both the benzyl protecting groups, for example with a palladium catalyst at about 1000 psi and 70°–100° C. However a stepwise hydrogenation is possible, as the O-protecting group can be removed selectively under mild conditions and by suitable choice, readily appovent to the skilled man, of the O- and N- protecting groups.

The compounds of formula (XIX) may themselves be prepared by reacting a monobenzylated dihydroxybenzene of formula (XX):

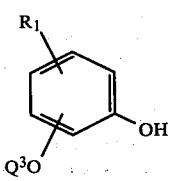

(XX)

as its sodium salt, with a chloro ester of formula (XXI):

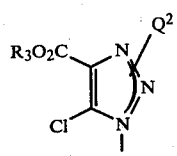

(XXI)

Although compounds of the formula (XVI) wherein $R_9$ is $C_{1-4}$ alkoxy $R_8$ may be prepared via these compounds it is preferred to prepare them directly by reaction of a compound of the formula (XXI) with a compound of the formula (XXII):

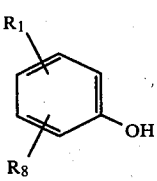

(XXII)

wherein the variables are as hereinbefore defined.

The salts of the compounds of the formula (I) may be prepared in the usual manner from the corresponding "free" compounds of the formula (I).

It is believed that the intermediates described above are all novel with the exception of compounds of formula (XXI) wherein $R_3$ is ethyl, and as such form an important portion of the present invention.

As previously stated, the compounds of formula (I) are active therapeutically.

Accordingly, this invention also provides a pharmaceutical composition comprising a compound of formula (I) as defined above, or a pharmaceutically acceptable salt thereof, and a pharmaceutically acceptable carrier.

Examples of suitable and preferred compounds for inclusion in such compositions are as previously discussed.

The compositions are of course adapted for administration to mammals especially human beings for the prophylaxis or treatment of diseases due to an allergic response.

Compounds of formula (I), which are active when given by the oral route, may be compounded in the form of syrups, tablets, capsules, pills and the like. Preferably, the compositions are in unit dosage form, or in a form in which the patient can administer to himself a single dosage. When the composition is in the form of a tablet, powder or lozenge, any pharmaceutical carrier suitable for formulating solid compositions may be used. Examples of such carriers are magnesium stearate, starch, lactose, glucose, sucrose, rice flour and chalk. The composition may also be in the form of an ingestible capsule (e.g. of gelatin) containing the compound; or in the form of a syrup, a liquid solution or a suspension. Suitable liquid pharmaceutical carriers include ethyl alcohol, glycerine, saline and water which may be compounded with flavouring or colouring agents to form syrups.

The compounds of this invention may also be administered by a non-oral route. In accordance with routine pharmaceutical procedure, the compositions may be formulated, for example for rectal administration as a suppository or for presentation in an injectable form in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, antioxidants or other preservatives, buffers solutes to render the solution isotonic with the blood, thickening agents, suspending agents or other pharmaceutically acceptable additives. Such forms will be presented in unit dosage form such as ampoules or disposable injection devices or in multi-dose forms such as a bottle from which the appropriate dose may be withdrawn, or as a solid form or concentrate which can be used to prepare an injectable formulation.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitable have diameters of less than 50 microns, preferably less than 10 microns. Where appropriate, small amounts of other anti-asthmatics and bronchodilators for example sympathomimetic amines such as isoprenaline, isoetharine, salbutamol, phenylephrine and ephedrine; xanthine derivatives such as theophylline and aminophylline; and corticosteroids such as prednisolone and adrenal stimulants such as ACTH may be included.

Compounds of general formula (I) may also be presented as an ointment, cream, lotion, gel, aerosol, or skin paint for topical application.

It is preferred that the compounds of this invention are administered by inhalation.

By way of example, in any of the preceding formulations a suitable dosage unit might contain 0.01 to 500 mgs of active ingredient, more suitably 1 to 500 mgs via the oral route, 0.01 to 1 mgs via inhalation. The effective dose of compound (I) depends on the particular compound employed, the condition of the patient and on the frequency and route of administration, but in general is in the range of from 0.001 mg/kg/day to 100 mg/kg inclusive of the patient's body weight.

As is common practice, the compositions will usually be accomplished by written or printed directions for use in the medical treatment concerned, in this case as an anti-allergic agent for the prophylaxis and treatment of for example, asthma, hay-fever, rhinitis or allergic eczema.

The following Examples illustrate the preparation and properties of compounds of this invention.

EXAMPLE 1

(a) 3-Benzyloxy-2-methylphenol

Anhydrous potassium carbonate (30.4 g.) was added to a stirred solution of 2-methylresorcinol (24.8 g) in N,N-dimethylformamide (DMF, 250 ml) and benzyl chloride (25.3 g) was added over 15 minutes. The mixture was heated to 80° C. and maintained at this temperature overnight with continued stirring. On cooling the DMF was removed in vacuo to give an oil which was partitioned between water and ether. The dried ethereal phase was evaporated and chromatographed on silica eluting with chloroform to give 9.78 g (23%) of the title compound of mp 58°–59° C. (Found; C, 78.16; H, 6.63; $C_{14}H_{14}O_2$ requires C, 78.48, H, 6.58%).

(b) Ethyl 1-benzyl-5-(3-benzyloxy-2-methylphenoxy)-v-triazole-4-carboxylate

A 50% dispersion of sodium hydride (1.68 g, 0.035 mole) was added to a stirred solution of 3-benzyloxy-2-methylphenol (7.5 g, 0.035 mole) in dry DMF (200 ml) and to the resulting sodium salt was added a solution of ethyl 1-benzyl-5-chloro-v-triazole-4-carboxylate (9.30 g; 0.035 mole) in dry DMF (20 ml). The reaction mixture was heated with stirring at 80° C. for 24 hours and then cooled. Removal of the DMF in vacuo gave a dark oil which was taken up in chloroform, washed with water and dried. Evaporation gave an oil which crystallized on standing. Recrystallization gave 10.27 g (66%) of product of mp 98°–99° C. (Found; C, 70.48; H, 5.76, N, 9.54; $C_{26}H_{25}N_3O_4$ requires C, 70.41; H, 5.68; N, 9.48%).

(c) Ethyl 5-(3-hydroxy-2-methylphenoxy)-1H-v-triazole-4-carboxylate

Hydrogenolysis of a solution of ethyl 1-benzyl-5-(3-benzyloxy-2-methylphenoxy)-v-triazole-4-carboxylate (10 g) in ethanol (300 ml) over 10% palladium on charcoal at 100° C. and 1000 psi resulted in a clean removal of both the O- and N-benzyl groups within 3 hours. On cooling and removal of the catalyst by filtration, evaporation of the solvent gave an oil which after filtration through a kiezelgel column in chloroform gave 4.20 g (71%) of product of mp 120°–122° C. (Found; C, 54.62; H, 5.04; N, 16.19; $C_{12}H_{13}N_3O_4$ requires C, 54.75; H, 4.98; N, 15.96%).

(d) 5-(3-Hydroxy-2-methylphenoxy)-1H-v-triazole-4-carboxylic acid

Hydrolysis of ethyl 5-(3-hydroxy-2-methylphenoxy)-1H-v-triazole-4-carboxylate (2 g) with 5% aqueous sodium hydroxide (30 ml) at 80° C. over 1 hour afforded the acid which was isolated from acidification of the cooled (0° C.) solution. Recrystallization from aqueous ethanol gave 1.47 g (82%) of material of mp 141°-143° C. (Found: C, 50.71; H, 3.85, N, 17.70; $C_{10}H_9N_3O_4$ requires: C, 51.06; H, 3.86; N, 17.87%).

(e) 6-Mesyloxy-5-methyl-9-oxo-1H,9H-benzopyrano[2,3-d]-v-triazole (i) To a solution of phosphoric oxide (21 g) in 98% methane sulphonic acid (90 g) at 60° C. was added 5-(3-hydroxy-2-methylphenoxy) 1H-v-triazole-4-carboxylic acid (2.8 g) with stirring and the mixture maintained at 100° C. After 22 hours at this temperature hplc monitoring showed the absence of starting material. The mixture was cooled, diluted with ice water and the product extracted into ethyl acetate. Evaporation of the dried extracts gave an oily solid which was recrystallized from ethanol in the presence of charcoal to give 1.39 g (40%) of the title compound of mp 183°-190° C. Further recrystallization gave material of mp 211°-212° C., δ(DMSO) 2.50 (3H, s); 3.58 (3H, s); 4.6 (broad exchangeable), 7.88 (2H, AB quartet J 9.0 Hz; Δν57 Hz), M+ 295.0265 ($C_{11}H_9N_3SO_5$) (Found: C, 44.65; H, 2.65 N, 13.75; $C_{11}H_9N_3SO_5$ requires C, 44.4; H; 3.05; N, 14.2%)

(ii) A similar treatment of 5-(3-mesyloxy-2-methylphenoxy)1H-v-triazole-4-carboxylic acid (0.1 g, mp 144° C., prepared from the hydroxy compound with $P_2O_5$ in methane sulphonic acid at 70° C.) gave, after recrystallization from ethanol, 0.07 g (74%) of cyclic product of mp 205°-207° C. and identical with that prepared above.

(f) 6-Mesyloxy-N-(4-methoxybenzyl)-5-methyl-9-oxo-9H-benzopyrano[2,3-d]-v-triazole The above mesylate (1.069 g; 0.0036 mole) was dissolved in anhydrous DMF (20 ml) and treated with anhydrous potassium carbonate (0.745 g; 0.0054 mole) and 4-methoxybenzyl chloride (0.6 g, slight excess). The mixture was stirred at room temperature for 24 hours after which time the solvent was removed in vacuo. Water and ethyl acetate were added to the residue and the phases separated. After evaporation of the dried organic phase the resulting oil was chromatographed to give 0.73 g (50%) of a 1:1 ratio of mixed isomers believed to be N-1 and N-2 derivatives. The aqueous phase gave 0.25 g of unchanged starting triazole. The methylene signals in the NMR spectrum occurred at δ(CDCl$_3$) 5.60 and 5.85 ppm.

(g) 6-Hydroxy-N-(4-methoxybenzyl)-5-methyl-9-oxo-9H-benzopyrano[2,3-d]-v-triazole The mixture of 4-methoxybenzyl triazoles (0.7 g) was treated with 1.25 M sodium hydroxide (70 ml) and ethanol (20 ml) added. After stirring at 80° C. for 5 hours the hydrolysis was complete by tlc and the reaction mixture was cooled and acidified at 0° C. The white solid which separated was filtered off, washed well with water and dried in vacuo over $P_2O_5$ to give 0.595 g (100%) of material of m.p. 219°-216° C. Recrystallization from ethanol gave mixed isomers of m.p. 229°-239° C.

(Found: C, 63.70; H, 4.12; N, 12.19; $C_{18}H_{15}N_3O_4$ requires: C, 64.09; H, 4.48; N, 12.46%)

(h) 6-{3-[4-(4-Chlorobenzyl)-1-piperazinyl]propyloxy}N-(4-methoxybenzyl)-5-methyl-9-oxo-9H-benzopyrano[2,3-d]-v-triazole A mixture of the above 4-methoxybenzyl isomers (168 mg) and 1-(4-chlorobenzyl)-4-(3-hydroxypropyl) piperazine (140 mg) in dry tetrahydrofuran (THF, 10 ml) was treated with triphenylphosphine (200 mg) and stirred for a few minutes at room temperature. A solution of diethyl azodicarboxylate (180 mg) in THF (2 ml) was then added and the mixture stirred at room temperature for 45 minutes. The solvent was removed in vacuo and a small volume of ethanol added to the residue. After standing several hours at 0° C. the solid which separated was filtered off and washed well with ethanol. Drying in vacuo gave 95 mg (32%) of the title compounds of m.p. 152°-158° C.

(i) 6-{3-[4-(4-Chlorobenzyl)-1-piperazinyl]propyloxy}-5-methyl-9-oxo-1H,9H,benzopyrano[2,3-d]-v-triazole

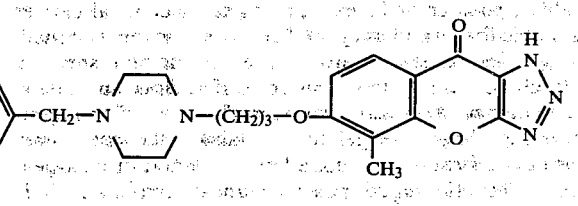

A solution of the mixed 4-methoxybenzyl isomers of the title compound (40 mg) in trifluoroacetic acid (2 ml) was stirred at 60° C. while the demethoxybenzylation was followed by hplc. After 7 hours the reaction was virtually complete and the mixture was cooled and water (2 ml) added. The blue-green solid which separated was filtered off and the clear filtrate diluted with more water and basified with dilute sodium hydroxide solution. After making acid with a minimum of acetic acid the cloudy solution was stood overnight at 4° C. and the product filtered off, washed well with water and dried to give 29 mg of product. Chromatography of this solid on silica, eluting first with chloroform and then with increasing concentrations of methanol up to 20% gave 26 mg (82%) of title compound as a pure material, m.p. 140° C. (foams), δ(d$_6$ acetone) 1.62 (2H, m); 2.28 (3H, s); 2.60 (4H, m); 2.88 (6H, m); 3.49 (2H, s); 4.10 (2H, t); 6.79 (1H, d, J 10 Hz); 7.31 (4H, s); 7.95 (1H, d, J 10 Hz).

REWORK OF EXAMPLE 1

Example 1, stages (f) to (i) were reworked to illustrate separation of N-1 and N-2 (4-methoxy benzyl) isomers, as new examples 1(f)R, 1(g)R, 1(i)R:

EXAMPLE 1(f)R

6-Mesyloxy-N-(4-methoxybenzyl)-5-methyl-9-oxo-9H-benzopyrano[2,3-d]-v-triazole

The above mesylate (7.00 g; 0.024 mole) was dissolved in anhydrous DMF (150 ml) and treated with anhydrous potassium carbonate (5.00 g; 0.036 mole) and 4-methoxybenzyl chloride (4.5 g, small excess). The mixture was stirred at room temperature for 72 hours after which time the solvent was removed in vacuo. Water and ethyl acetate were added to the residue and the phases separated. After evaporation of the dried organic phase the resulting oil was chromatographed to give 6.32 g (63%) of a 1:1 mixture of mixed isomers believed to be the N-1 and N-2 derivatives. Rechromatography of a small sample of this mixture afforded pure samples of the individual isomers.

N-1 isomer mp (EtOH/CHCl$_3$) 149°–153° C., $\nu_{max}$(mull) 1678, 1603, 1520, 1512, 1363 cm$^{-1}$; δ(CDCl$_3$) 2.55 (3H, s); 3.27 (3H, s); 3.72 (3H, s), 5.88 (2H, s); 6.81 (2H, d, J 9 Hz); 7.38 (1H, d, J 9 Hz); 7.45 (2H, d, J 9 Hz); 8.20 (1H, d, J 9 Hz), M+ 415.0809 (C$_{19}$H$_{17}$N$_3$O$_6$S). (Found; C, 54.7; H, 4.3; N, 9.9; S, 7.55; C$_{19}$H$_{17}$N$_3$O$_6$S requires; C, 54.95; H, 4.1; N, 10.1; S, 7.7%).

N-2 isomer mp (EtOH/CHCl$_3$) 170°–172° C., $\nu_{max}$ (mull) 1680, 1615, 1545, 1518 cm$^{-1}$ δ(CDCl$_3$) 2.52 (3H, s); 3.28 (3H, s); 3.78 (3H, s); 5.65 (2H, s); 7.15 (4H, AB quartet, Δν45 Hz, J 10 Hz); 7.42 (1H, d, J 10 Hz); 8.30 (1H, d, J 10 Hz) (Found; C, 54.7; H, 4.35; N, 10.1; s, 7.49; C$_{19}$H$_{17}$N$_3$O$_6$S requires; C, 54.95; H, 4.1; N, 10.1%).

EXAMPLE 1g (i) 6-Hydroxy-1-(4-methoxybenzyl)-5-methyl-9-oxo-9H-benzopyrano[2,3-d]-v-triazole

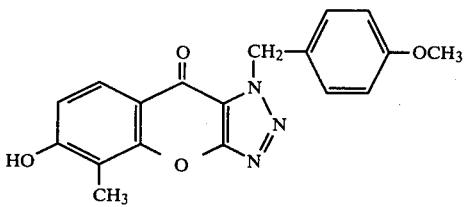

Hydrolysis of 6-methanesulphonyloxy-1-(4-methoxybenzyl)-5-methyl-9-oxo-9H-benzopyrano[2,3-d]-v-triazole (1.494 g) with 5% aqueous sodium hydroxide (153 ml) and ethanol (40 ml) at 80° C. for 3 hours afforded the hydroxy compound which was isolated by acidification of the cooled, yellow solution. Recrystallization from ethanol gave 0.592 g (49%) of white material, mp 257°–8° C. (dec) $\nu_{max}$ (mull) 1615, 1660, 3100 cm$^{-1}$, δ(DMSO-d$_6$), 2.30 (3H, s), 3.75 (3H, s), 5.89 (2H, s), 7.03 (1H, d, J 9 Hz), 7.13 (4H, ABq, Δν42 Hz, J 9 Hz), 7.92 (1H, d, J 9 Hz), 11.0 (1H, broad, exchanges with D$_2$O). (Found, C, 64.17; H, 4.72 N, 12.46; C$_{18}$H$_{15}$N$_3$O$_4$ requires C, 64.09; H, 4.48, N, 12.46%).

(ii) 6-Hydroxy-2-(4-methoxybenzyl)-5-methyl-9-oxo-9H-benzopyrano[2,3-d]-v-triazole

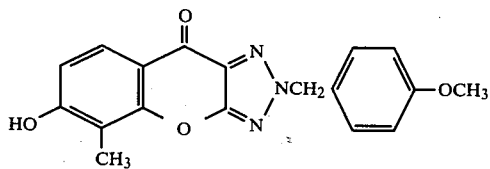

Hydrolysis of 6-methanesulphonyloxy-2-(4-methoxybenzyl)-5-methyl-9-oxo-9H-benzopyrano[2,3-d]-v-triazole (1.22 g) with 5% aqueous sodium hydroxide (125 ml) and ethanol (35 ml) at 80° C. for 3 hours afforded the hydroxy compound which was isolated by acidification of the cooled yellow solution. Recrystallization from ethanol gave 0.477 g (47%) of white material, mp 264°–5° C. (dec) $\nu_{max}$ (mull) 1605, 1670, 3215 cm$^{-1}$, δ(DMSO-d$_6$), 2.25 (3H, s), 3.74 (3H, s), 5.70 (2H, s), 6.94 (1H, d, J 9 Hz), 7.13 (4H, ABq, Δν40 Hz, J 9 Hz), 7.88 (1H, d, J 9 Hz), 10.90 (1H, s, exchanges with D$_2$O). (Found, C, 64.06; H, 4.68, N, 12.44; C$_{18}$H$_{15}$N$_3$O$_4$ requires; C, 64.09; H, 4.48; N, 12.46%).

EXAMPLE (h) R 6-(3-[4-(4-chlorobenzyl)-1-piperazinyl]propyloxy)-1-(4-methoxybenzyl)-5-methyl-9-oxo-9H-benzopyrano[2,3-d]-v-triazole A mixture of N-1 and N-3 isomers of 6-Hydroxy-N-(4-methoxybenzyl)-5-methyl-9-oxo-9H-benzopyrano[2,3-d]-v-triazole (1.922 g; 5.7 mmole, 1:1 ratio) and 1-(4-chlorobenzyl)-4-(3-hydroxypropyl)piperazine (1.62 g; 5.8 mmole) in dry tetrahydrofuran (THF, 80 ml) was reated with triphenylphosphine (2.40 g) and stirred at room temperature for a few minutes. A solution of diethylazodicarboxylate (2.16 g) in dry THF (15 ml) was added and the mixture stirred at room temperature for 1½ hours. The solvent was removed in vacuo to give a foam which crystallized on warming with ethanol (45 ml). After cooling in ice the solid was filtered off and dried to give 1.36 g of mixed N-1 and N-2 isomers with the N-1 isomer predominating. Recrystallization from ethanol afforded pure N-1 isomer which has mp (MeOH/CHCl$_3$) 152°–155° C., $\nu_{max}$ (mull) 1665, 1610, 1530, 1510 cm$^{-1}$, δ(CDCl$_3$), 1.98 (2H, quintet, J 6 Hz); 2.33 (3H, s); 3.47 (10H, m); 3.30 (2H, s); 3.69 (3H, s); 4.12 (2H, t, J 6 Hz); 5.86 (2H, s); 6.80 (2H, d, J 9 Hz); 6.95 (1H, d, J 9 Hz); 7.22 (4H, s); 7.44 (2H, d, J 9 Hz); 8.12 (1H, d, J 9 Hz), M+ 587.2306 (C$_{32}$H$_{34}$N$_5$O$_4$Cl); (Found; C, 65.29; H, 5.66; N, 11.62; C$_{32}$H$_{34}$N$_5$O$_4$Cl requires; C, 65.35; H, 5.83; N, 11.91%).

Evaporation of the ethanol filtrate above and chromatography on silica eluting with chloroform separated the slower running N-2 isomer to give 1.610 g of material of mp (MeOH/CHCl$_3$) 142°–143° C., $\nu_{max}$ (mull) 1670, 1612, 1542, 1515 cm$^{-1}$, δ(CDCl$_3$) 2.00 (2H, quintet, J 6 Hz); 2.30 (3H, s); 2.47 (10H, m); 3.41 (2H, s); 3.72 (3H, s); 4.12 (2H, t, J 6 Hz); 5.58 (2H, s); 6.82 (2H, d, J 9 Hz); 6.90 (1H, d, J 9 Hz); 7.22 (4H, s); 7.37 (2H, d, J 9 Hz); 8.17 (1H, d, J 9 Hz), M+ 587.2337 (C$_{32}$H$_{34}$N$_5$O$_4$Cl); (Found; C, 65.08; H, 5.56; N, 11.77, C$_{32}$H$_{34}$N$_5$O$_4$Cl requires: 65.35; H, 5.83; N, 11.91%).

Total yield of mixed isomers was 2.97 g (89%).

6-(3-[4-Chlorobenzyl)-1-piperazinyl]propyloxy)-5-methyl-9-oxo-1H,9H,benzopyrano[2,3-d]-v-triazoles

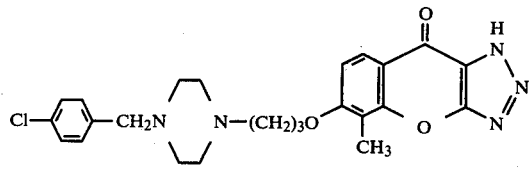

A solution of the mixed 4-methoxybenzyl isomers of the title compound (1.77 g) in trifluoroacetic acid (100 ml) was stirred at 65° C. for 3½ hours and then cooled. After removal of the trifluoroacetic acid in vacuo water was added and the pH brought to 9 with aqueous sodium hydroxide solution. After reacidification with acetic acid the mixture was maintained at 0° C. overnight and the solid filtered off, washed with water and dried to give 2.010 g of crude solid. Chromatography on silica eluting first with chloroform gave 0.662 g of mono trifluoroacetate salt of mp 134° C. (approx) (MeOH), δ(DMSO-d$_6$), 2.18 (2H, m), 2.36 (3H, s), 2.75 (4H, broad s); 3.20 (6H, broad s); 3.70 (2H, s); 4.25 (2H, t); 7.21 (1H, d, J 9 Hz); 7.42 (4H, s); 8.10 (1H, d, J 9 Hz).

(Found: C, 52.7; H, 4.75; N, 11.55; C$_{24}$H$_{26}$N$_5$ClO$_3$.CF$_3$CO$_2$H. 0.5 H$_2$O requires; C, 52.85; H, 4.83; N, 11.85%).

Further elution with methanol gavoe 0.550 g of material of mp 232°-235° C. (dec) thought to be the free zwitterionic compound. Reaction with sodium hydroxide afforded the sodium salt. (Found: C, 58.65; H, 5.65; N, 13.7; C$_{24}$H$_{25}$N$_5$ClO$_3$Na requires; C, 58.85; H, 5.15; N, 14.3%).

EXAMPLE 2

(a) 1-Carboethoxy-4-(4-methylbenzyl)piperazine

Ethyl N-piperazinocarboxylate (10 g; 0.063 mole) and anhydrous potassium carbonate (13 g; 0.094 mole) in dry butanone (100 ml) were stirred at reflux and a solution of 4-methylbenzyl chloride (8.8 g; 0.063 mole) in butanone (10 ml) was added dropwise over 1 hour.

After a further 3 hours at reflux the mixture was cooled and the solvent removed in vacuo to give a yellow oil. Conversion to the hydrochloride gave 13.1 g (70%) of material of mp (EtOH/Et$_2$O) 204°-206° C. (Found; C, 60.65; H, 7.35; N, 9.6; Cl, 11.9; C$_{15}$H$_{23}$N$_2$O$_2$Cl requires; C, 60.3; H, 7.75; N, 9.4; Cl, 11.85%).

(b) N-(4-methylbenzyl)piperazine

The above ester (13 g; 0.0435 mole), sodium hydroxide solution (20% w/v, 100 ml) and 2-ethoxyethanol (25 ml) were stirred at reflux for 18 hours, cooled to 70° C. and acidified with concentrated hydrochloric acid. After the vigorous effervescence ceased the mixture was cooled, rebasified and extracted with ether. The dried extracts were evaporated to an oily solid which was chromatographed to give 2.88 g (35%) of title compound as an homogeneous oil.

(c) 1-(3-Hydroxypropyl)-4-(4-methylbenzyl)piperazine

A mixture of the above piperazine (2.58 g, 0.0136 mole), 3-bromopropanol (1.9 g, 0.0136 mole) and anhydrous potassium carbonate (2.30 g) in dry butanone (50 ml) was stirred at reflux over night. The cooled mixture was evaporated in vacuo and the residue partitioned between water and ether. Evaporation of the dried organic phase gave the product as a yellow oil which crystallized on standing to give 3.18 g (94%) of material of mp (petroleum [bp 40°-60°]) 62°-63° C. (Found; C, 72,35; H, 10.15; N, 11.55; C$_{15}$H$_{24}$N$_2$O requires; C, 72-55; H, 9.75; N, 11.3%).

(d) 6-{3-[4-(4-Methylbenzyl)-1-piperazinyl]propyloxy}-N-(4-methoxybenzyl)-5-methyl-9-oxo-9H-benzopyrano[2,3-d]-v-triazole A mixture of the 4-methoxybenzyl isomers from Example 1 g (0.674 g; 2 mmole) and 1-(3-hydroxypropyl)-4-(4-methylbenzyl)piperazine (0.600 g, slight excess) in dry THF (30 ml) was treated with triphenyl phosphine (0.800 g) followed by a solution of diethyl azodicarboxylate (0.720 g) in dry THF (5 ml). After stirring for 1½ hours the solvent was evaporated in vacuo to give a sticky solid. Trituration with ethanol gave 0.432 g (38%) of the N-1 isomer of mp (methanol) 150°-152° C. δ(CDCl$_3$) 2.00(2H, quintet, J 6 Hz); 2.30 (3H, s); 2.35 (3H, s); 2.48(10H, m); 3.43(2H, s); 3.71 (3H, s); 4.13 (2H, t, J 6 Hz); 5.87 (2H, s); 6.81 (2H, d, J 9 Hz); 6.96 (1H, d, J 9 Hz); 7.12 (4H, AB quartet); 7.45 (2H, d J 9 Hz); 8.11 (1H, d, J 9 Hz). M+ 567.2866 (C$_{33}$H$_{37}$N$_5$O$_4$); (Found; C, 69.45; H, 6.2; N, 12.6; C$_{33}$H$_{37}$N$_5$O$_4$ requires; C, 69.8; H, 6.55; N, 12.35%).

Evaporation of the ethanol solution followed by chromatography of the residue gave 0.51 g (45%) of N-2 isomer of mp (MeOH) 125°-127° C. δ(CDCl$_3$) 2.00 (2H, quintet J 6 Hz); 2.30 (6H, s); 2.45 (10H, m); 3.42 (2H, s); 3.73 (3H, s); 4.12 (2H, t, J 6 Hz); 5.59 (2H, s); 6.85 (2H, d, J 9 Hz); 6.93 (1H, d, J 9 Hz); 7.12 (4H, AB quartet); 7.40 (2H, d, J 9 Hz); 8.20 (1H, d, J 9 Hz). M+ 567.2831 (C$_{33}$H$_{37}$N$_5$O$_4$); (Found; C, 69.9; H, 6.4; N, 12.2; C$_{33}$H$_{37}$N$_5$O$_4$ requires; C, 69.8; H, 6.55; N, 12.35%).

(e) 6-{3-[4-(4-Methylbenzyl)-1-piperazinyl]propyloxy}-5-methyl-9-oxo-1H,9H-benzopyrano[2,3-d]-v-triazole

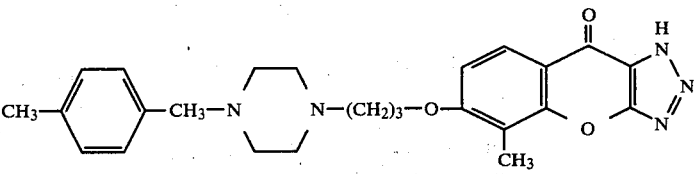

A solution of the N-1 (4-methoxybenzyl) derivative of the title compound (400 mg) in trifluoroacetic acid (20 ml) was stirred at 62° C. for 7½ hours when hplc indicated complete reaction. The cooled solution was diluted with water and made alkaline with sodium hydroxide. After reacidification with acetic acid the suspension was stood at 4° C. overnight and filtered. Chromatography of the residue on SiO$_2$ eluting with 15% methanol in chloroform afforded 0.22 g (70%) of the title compound. After trituration with hot ethyl acetate it had mp 224°-226° C. (dec), ν$_{max}$ (mull) 1645, 1605, 1480, 1275 cm$^{-1}$, δ(d$_4$-MeOH) 2.04 (3H, s); 2.18 (2H, m); 2.28 (3H, s); 2.92 (4H, m); 3.38 (6H, m); 3.67 (2H, s); 3.90 (2H, m); 6.32 (1H, d, J 8.5 Hz); 7.18 (4H, AB quartet J 8.5 Hz, Δν11 Hz); 7.58 (1H, d, J 8.5 Hz). M+ 447.2266 (C$_{25}$H$_{29}$N$_5$O$_3$). (Found; C, 65.4; H, 6.3; N, 15.15; C$_{25}$H$_{29}$N$_5$O$_3$.0.5H$_2$O requires; C, 65.75; H, 6.6; N 15.35%).

EXAMPLE 3

(a) 6-{3-[4-(2-Chlorobenzyl)-1-piperazinyl]propyloxy}-N-(4-methoxybenzyl)-5-methyl-9-oxo-9H-benzopyrano[2,3-d]-v-triazole A mixture of the 4-methoxybenzyl isomers from Example 1g) (0.674 g; 2 mmole) and 1-(2-chlorobenzyl)-4-(3-hydroxypropyl) piperazine (0.540 g, slight excess, prepared in a similar manner to the 4-methyl analogue described above) in dry THF (30 ml) were treated with triphenylphosphine (0.800 g) followed by diethyl azodicarboxylate (0.720 g). After stirring for 1½ hours at room temperature the solvent was removed in vacuo and the resulting foam triturated with ethanol. Filtration gave 0.515 g (44%) of N-1 isomer of mp (EtOH/CHCl$_3$) 163°-166° C., ν$_{max}$ (mull) 1665, 1605, 1525, 1510, 1265, 1245 cm$^{-1}$, δ(CDCl$_3$) 2.02 (2H, quintet, J 6 Hz); 2.38 (3H, s); 2.53 (10H, m); 3.61 (2H, s); 3.72 (3H, s); 4.15 (2H, t, J 6 Hz); 5.88 (2H, s); 6.98 (1H, d, J 9 Hz); 7.10-7.48 (4H, m); 7.20 (4H, AB quartet, Δν59 Hz; J 9 Hz); 8.12 (1H, d, J 9 Hz). M+ 587.2310 (C$_{32}$H$_{34}$N$_5$O$_4$Cl). (Found: C, 65.0; H, 5.5; N, 12.1; C$_{32}$H$_{34}$N$_5$O$_4$Cl requires: C, 65.35; H, 5.85; N,11.9%).

Chromatography of the evaporated ethanol mother liquors afforded 0.291 g (25%) of the N-2 isomer of mp (EtOH) 83°-85° C., $v_{max}$ (mull) 1680, 1605, 1545, 1515 cm$^{-1}$, δ(CDCl$_3$) 2.00 (2H, quintet, J 6 Hz); 2.31 (3H, s); 2.52 (10H, m); 3.60 (2H, s); 2.76 (3H, s); 4.13 (2H, t, J 6 Hz); 5.60 (2H, s); 6.85 (2H, d, J 9 Hz); 6.93 (1H, d, J 9 Hz); 7.09-7.50 (4H, m); 7.39 (2H, d, J 9 Hz); 8.20 (1H, d, J 9 Hz). M+ 587.2254 (C$_{32}$H$_{34}$N$_5$O$_4$Cl) (Found: C, 65.3; H, 5.7; N, 11.85: C$_{32}$H$_{34}$N$_5$O$_4$Cl requires: C, 65.35; H, 5.85; N, 11.9%).

(b) 6-{3-[4-(2-Chlorobenzyl)-1-piperazinyl]propyloxy}-5-methyl-9-oxo-1H,9H-benzopyrano[2,3-d]-v-triazole

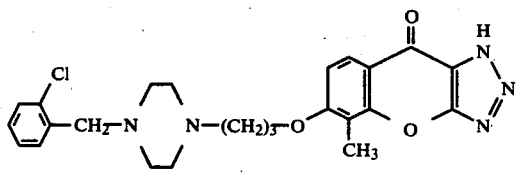

A solution of the N-1 (4-methoxybenzyl) derivative of the title compound (0.338 g) in trifluoroacetic acid (18 ml) was stirred at 65° C. for 4½ hours and the cooled, green solution was diluted with water. After basifying with sodium hydroxide the pH was adjusted to 4.5 with acetic acid and the suspension stood overnight at 4° C. Filtration and chromatography of the residue gave 0.177 g (66%) of the title product of mp 248°-250° C. after trituration with ethyl acetate. It had $v_{max}$ (mull) 1655, 1485, 1280 cm$^{-1}$, δ(TFA-d$_1$) 2.48 (3H, s); 2.53 (2H, m); 3.62-4.50 (12H complex multiplet); 4.77 (2H, s); 7.18 (1H, d, J 9 Hz); 7.53 (4H, distorted s); 8.37 (1H, d, J 9 Hz). M+ 467.1734 (C$_{24}$H$_{26}$N$_5$O$_3$Cl). (Found: C, 58.6; H, 5.55; N, 13.3; C$_{24}$H$_{26}$N$_5$ClO$_3$. 1.5 H$_2$O requires: C. 58.25; H, 5.9; N, 14.15%).

This material may also be prepared by an analogous deprotection of the N-2 (4-methylbenzyl) derivative. In this instance the yield of material of mp 240°-243° C. (dec) is 67%.

The monotrifluoroacetate salt has m.p. 134° (approx) (Found; C, 52.75; H, 4.85; N, 12.2; C$_{24}$H$_{26}$N$_5$ClO$_3$.CF$_3$CO$_2$H. 0.5H$_2$O requires; C, 52.85; H, 4.8; N, 11.85%).

The sodium salt was prepared with aqueous sodium hydroxide. (Found; C, 58.4; H, 5.55; N, 14.15, C$_{24}$H$_{25}$N$_5$ClO$_3$Na requires; C, 58.85; H, 5.15; N, 14.3%).

EXAMPLE 4

(a) 6-{3-[4-(4-Methoxybenzyl)-1-piperazinyl]propyloxy}-N-(4-methoxybenzyl)-5-methyl-9-oxo-9H-benzopyrano[2,3-d]-v-triazole A mixture of the 4-methoxybenzyl isomers from Example 1g) (0.674 g, 2 mmole) and 1-(3-hydroxypropyl)-4-(4-methoxybenzyl) piperazine (0.55 g, slight excess, mp 58°-59° C., prepared in a similar manner to the 4-methyl analogue described above) in dry THF (30 ml) was treated with triphenylphosphine (0.800 g) and diethyl azodicarboxylate (0.720 g) and the mixture stirred for 1½ hours at room temperature. Evaporation of the solvent in vacuo furnished a semi solid residue which gave 0.432 g (37%) of the N-1 derivative on trituration with cold ethanol. After recrystallization from methanol/chloroform it had mp 157°-158° C., $v_{max}$ (mull) 1678, 1620 cm$^{-1}$, δ(CDCl$_3$) 1.98 (2H, quintet, J 6 Hz); 2.34 (3H, s); 2.47 (10H, m); 3.40 (2H, s); 3.70 (3H, s); 3.75 (3H, s); 4.12 (2H, t, J 6 Hz); 5.86 (2H, s); 6.80 (4H, d, J 9 Hz); 6.96 (1H, d, J 9 Hz); 7.18 (2H, d, J 9 Hz); 7.45 (2H, d, J 9 Hz); 8.11 (1H, d, J 9 Hz). M+ 583.2751 (C$_{33}$H$_{37}$N$_5$O$_5$). (Found: C, 67.7; H, 6.25; N, 12.1; C$_{33}$H$_{37}$N$_5$O$_5$ requires: C, 67.9; H, 6.4; N, 12.0%).

The ethanol mother liquors were evaporated to dryness and chromatographed to give 0.70 g (60%) of mixed isomers of mp 138°-141° C. shown by NMR to be 79% N-2; 21% N-1.

The N-2 isomer had δ(CDCl$_3$) 2.00 (2H, quintet, J 6 Hz); 2.30 (3H,s); 2.47 (10H, m); 3.42 (2H, s); 3.78 (6H, s); 4.12 (2H, t, J 6 Hz); 5.60 (2H, s); 6.80 (2H, d, J 9 Hz); 6.86 (2H, d, J 9 Hz); 6.93 (1H, d, J 9 Hz); 7.19 (2H, d, J 9 Hz); 7.39 (2H, d, J 9 Hz); 8.19 (1H, d, J 9 Hz). M+583.2796 (C$_{33}$H$_{37}$N$_5$O$_5$). (Found: C, 68.35; H, 6.05; N, 12.05; C$_{33}$H$_{27}$N$_5$O$_5$ requires: C, 67.9; H, 6.4: N, 12.0%).

(b) 6-{3-[4-(4-Methoxybenzyl)-1-piperazinyl]-propyloxy}-5-methyl-9-oxo-1H,9H-benzopyrano[2,3-d]-v-triazole

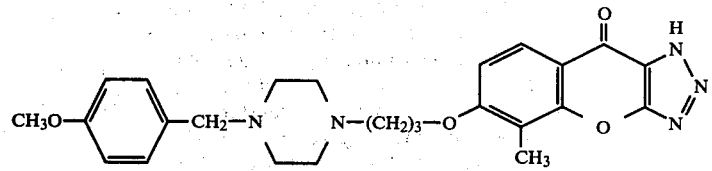

A solution of the N-1 (4-methoxybenzyl)derivative of the title compound (300 mg) in trifluoroacetic acid (15 ml) was heated to 65° C. for 3 hours and the cooled solution diluted with water. Excess sodium hydroxide solution was added and the pH adjusted to 4.5 with acetic acid. After standing at 4° C. overnight the solid was filtered off and chromatographed to give 0.220 g (92%) of the title compound of mp 234°-237° C. (dec) after trituration with ethyl acetate. It had $v_{max}$ (mull) 1650, 1605, 1515, 1485 and 1270 cm$^{-1}$, δ(DMSO) 2.00 (2H, quintet); 2.20 (3H,s); 2.78 (10H, m); 3.60 (2H, s); 3.66 (3H, s); 4.06 (2H, t); 6.78 (2H, d, J 9 Hz); 6.92 (1H, d, J 9 Hz); 7.16 (2H, d, J 9 Hz); 7.88 (1H, d, J 9 Hz); 8.39 (2H, broad, exchangeable). M+463.2174 (C$_{25}$H$_{29}$N$_5$O$_4$). (Found: C, 62.5; H, 6.35; N, 14.15; C$_{25}$H$_{29}$N$_5$O$_4$. H$_2$O requires: C, 62.35; H, 6.5: N, 14.55%)

EXAMPLE 5

(a) 6-{3-[4-(2-Pyridylmethyl)-1-piperazinyl]-propyloxy}-N-(4-methoxybenzyl)-5-methyl-9-oxo-9H-benzopyrano[2,3-d]-v-triazole A mixture of the 4-methoxybenzyl isomers from Example 1g) (0.674 g, 2 mmole) and 1-(3-hydroxypropyl)-4-(2-pyridylmethyl)piperazine (0.570 g, prepared in a similar manner to the 4-methyl analogue described above) in dry THF (30 ml) was treated with triphenylphosphine (0.800 g) and diethyl azodicarboxylate (0.720 g) and the mixture stirred at room temperature for 1½ hours. Evaporation of the solvent in vacuo afforded a sticky solid.* Yield 0.408 g (37%) of the N-1 derivative of mp 145°-152° C. (dec), δ(CDCl$_3$), 2.02 (2H, quintet, J 6 Hz); 2.37 (3H, s); 2.52 (10H, m); 3.63 (2H, s); 3.72 (3H, s); 4.12 (2H, t, J 6 Hz); 5.86 (2H, s); 6.80 (2H, d, J 9 Hz); 6.87 (1H, d, J 9 Hz); 7.10 (1H, m); 7.35 (1H, d, J 7 Hz); 7.46 (2H, d, J 9 Hz); 7.60 (1H, dt, J 7.5 Hz; 1.6 Hz); 8.11 (1H, d, J 9 Hz); 8.51 (1H, d, J 4.5 Hz). M+554.2652 ($C_{31}H_{34}N_6O_4$).

\* which on trituration with ethanol (15 ml) gave a white solid

The ethanol mother liquor was evaporated to dryness and chromatographed to give 0.73 g (66%) of predominantly (84%) N-2 isomer, δ(CDCl3) 2.02 (2H, quintet, J 6 Hz); 2.30 (3H, s); 2.52 (10H, m); 3.63 (2H, s); 3.72 (3H, s); 4.13 (2H, t, J 6 Hz); 5.58 (2H, s); 6.86 (2H, d, J 9 Hz); 6.92 (1H, d, J 9 Hz); 7.10 (1H, m); 7.36 (1H, d, J ≃7.5 Hz); 7.39 (2H, d, J 9 Hz); 7.60 (1H, d, t, J 7.5, 1.5 Hz); 8.19 (1H, d, J 9 Hz); 8.52 (1H, d, J 4.5 Hz).

(b) 6-{3-[4-(2-Pyridylmethyl)-1-piperazinyl]-propyloxy}-5-methyl-9-oxo-1H,9H-benzopyran-[2,3-d]-v-triazole

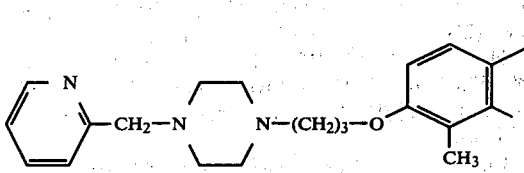

A solution of the enriched N-2 (4-methoxybenzyl) derivative of the title compound (0.710 g) in trifluoroacetic acid (35 ml) was heated at 65° C. for 5½ hours and the cooled solution diluted with water. The solution was made alkaline with dilute sodium hydroxide solution and then strongly acidified with hydrochloric acid and evaporated to dryness in vacuo. The residue was thoroughly extracted with ethanol to give 0.690 g of the title compound as its dihydrochloric acid salt. After conversion to the free base the material was chromatographed on silica to give 0.25 g (45%) of material of mp (MeOH) 236°-237° C., $v_{max}$ (mull) 1640, 1615 cm$^{-1}$, δ(CDCl3-d6-DMSO) 2.19 (2H, m); 2.33 (3H, s); 2.91 (10H, m); 3.78 (2H, s); 4.22 (2H, t); 6.93 (1H, d); 7.10-7.76 (3H, m); 8.02 (1H, d); 8.50 (1H, d). M+434.2089 ($C_{23}H_{26}N_6O_3$). (Found: C, 63.3; H, 5.9; N, 19.35; $C_{23}H_{26}N_6O_3$ requires C, 63.6; H, 6.05; N, 19.35%)

EXAMPLE 6

(a) Ethyl 1-benzyl-5-(3-methoxyphenoxy)-v-triazole-4-carboxylate

A 50% dispersion of sodium hydride in mineral oil (6.40 g, 0.13 mole) was added to a stirred solution of 3-methoxyphenol (16.40 g, 0.13 mole), in dry DMF (500 ml) and to the resulting sodium salt was added ethyl 1-benzyl-5-chloro-v-triazole-4-carboxylate (35.0 g, 0.13 mole). The reaction mixture was heated with stirring at 70° C. for 21 hours and cooled.

Removal of the DMF in vacuo gave a brown oil which was taken up in ether, washed with 1 M sodium hydroxide solution, water and brine and dried (MgSO4). Evaporation gave a red oil which crystallized on trituration with ether/petrol ether 40°-60° C. (1:1).

Recrystallisation from ether/petrol ether 60°-80° C. gave 33.75 g (53%) of product of mp 52°-53° C. (Found: C, 64.51; H, 5.27; N, 12.05; $C_{19}H_{19}N_3O_4$ requires: C, 64.58; H, 5.42; N, 11.89%)

(b) Ethyl 5-(3-methoxyphenyoxy)-1H-v-triazole-4-carboxylate

Hydrogenolysis of a solution of ethyl 1-benzyl-5-(3-methoxyphenoxy)-v-triazole-4-carboxylate (17.27 g) in ethanol (300 ml), over 10% palladium on charcoal at 100° C. and 1000 psi resulted in clean removal of the N-benzyl group in 2.5 hours. On cooling and removal of the catalyst by filtration, evaporation of the solvent gave an orange oil which crystallised on trituration.

Recrystallisation from ethanol/water gave 9.16 g (71%) of product of mp 104°-5° C. (Found: C, 54.92; H, 4.88; N, 15.71; $C_{12}H_{13}N_3O_4$ requires: C, 54.75; H, 4.98; N, 15.96%)

(c) 5-(3-Methoxyphenoxy)-1H-v-triazole-4-carboxylic acid

Hydrolysis of ethyl 5-(3-methoxyphenoxy)-1H-v-triazole-4-carboxylate (9.10 g), with 5% aqueous sodium hydroxide (110 ml), at 80° C. for 1 hour afforded the acid which was isolated after acidification of the cooled (0° C.) solution. Recrystallisation from ethylacetate/petrol ether 40°-60° C. gave 6.20 g (76%) of material of mp 133-4° C. (dec). (Found: C, 51.31; H, 3.60; N, 17.88. $C_{10}H_9N_3O_4$ requires: C, 51.07; H, 3.86; N, 17.86%)

(d) 6-Methoxy-9-oxo-1H,9H-benzopyrano[2,3-d]-v-triazole and 8-methoxy-9-oxo-1H,9H-benzopyrano[2,3-d]-v-triazole

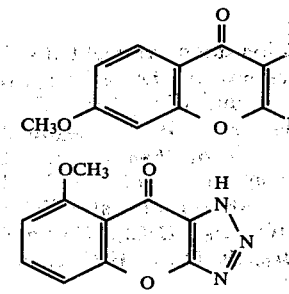

To a solution of phosphoruspentoxide (40 g) in 98% methane sulphonic acid (100 g) at 80° C. was added 5-(3-methoxyphenoxy)-1H-v-triazole-4-carboxylic acid (5.50 g) with vigorous stirring and the brown solution maintained at 80° C. After 4 hours hplc monitoring showed the absence of starting material. The solution was cooled, diluted with ice water and left to stand overnight. The pink precipitate was collected by filtration to yield 4.1 g, (75%) of the 6-methoxy and 8-methoxy mixed isomers in the ratio 2:1 respectively. The pure isomers could be separated by fractional crystallisation from ethanol.

Data for pure 6-methoxy isomer mp 207-1° C. (dec), $v_{max}$ (mull) 1585, 1615, 1640, 1655 cm$^{-1}$, δDMSOd6, 3.94 (3H, s), 7.09 (1H, dd, J 2 & 7 Hz); 7.27 (1H, d, J 2 Hz); 8.12 (1H, d, J 7 Hz). (Found: C, 54.97; H, 3.54; N, 19.51; $C_{10}H_7N_3O_3$ requires: C, 55.30; H, 3.25; N, 19.35%). M+=217.0494, 217.0494 ($C_{10}H_7N_3O_3$).

Data for pure 8-methoxy isomer mp 258-60° C., $v_{max}$ (mull) 1550, 1610, 1658, 1670, 3130 cm$^{-1}$, δDMSOd6; 3.92 (3H, s); 7.06 (1H, dd, J 8

Hz); 7.24 (1H, dd, J 8 Hz); 7.77 (1H, t, J 8 Hz) (Found: C, 55.31; H, 3.29; N, 19.64; $C_{10}H_7N_3O_3$ requires: C, 55.30; H, 3.25; N, 19.35%) $M^+=217.0487$ ($C_{10}H_7N_3O_3$).

(e) 6-Hydroxy-9-oxo-1H,9H-benzopyrano[2,3-d]-v-triazole

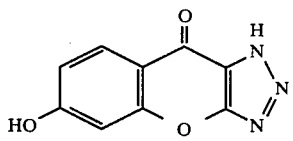

A 50% dispersion of sodium hydride (4.30 g, 0.09 M) was added to a stirred solution of ethenethiol (5.46 g, 0.09 m) in dry DMF (90 ml) and the resulting sodium salt was added 6-methoxy-9-oxo-1H,9H-benzopyrano[2,3-d]-v-triazole (2.25 g., 0.01 m). The mixture was heated, with stirring to 120° C. for 1.5 hours when TLC showed no starting material. The reaction was cooled and poured into ice water. The product was solated by acidification of the solution. Recrystallisation from aqueous DMF gave 1.80 g (85%) of material, mp 300° C. (dec), $v_{max}$ (mull) 1550, 1580, 1650, 3215 cm$^{-1}$, δDMSDd6; 6.94 (2H, m); 8.08 (1H, d, J 9 Hz); 11.01 (1H, s, exchanges with $D_2O$); $M^+=203.0337$ ($C_9H_5N_3O_3$).

(f) 6-Hydroxy-N-(4-methoxybenzyl)-9-oxo-9H-benzopyrano[2,3-d]-v-triazole

6-Hydroxy-9-oxo-1H,9H-benzopyrano[2,3-d]-v-triazol (2.37 g, 0.012 m), was dissolved in dry DMF (50 ml) and treated with anhydrous potassium carbonate (3.23 g, 0.023 M) and 4-methoxybenzylchloride (1.80 g, 0.012 M). The mixture was stirred at room temperature for 24 hours after which time the solvent was removed in vacuo. The residue was dissolved in water, acidified with 5 M HCl and extracted with ethyl acetate. After evaporation of the dried, organic phase, the resulting yellow oil was chromatographed to give 2.20 g (58%) of a 1:1 ratio of mixed isomers believed to be N-1 and N-2 derivatives. The methylene signals in the NMR spectrum occurred at δ(DMSOd6), 5.78 and 5.90 ppm. The pure N-1 isomer could be separated by column chromatography.

N-1 Isomer mp 230-1° C., $v_{max}$ (mull) 1605, 1640, 1660 cm$^{-1}$, δ(DMSOd$_6$) 3.74 (3H, s); 5.90 (2H, s); 6.93 (2H, m); 7.13 (4H, ABq, Δv33 Hz, J 9 Hz); 8.05 (1H, d, J 9 Hz); 11.14 (1H, s, exchanges $D_2O$). (Found: C, 63.63; H, 4.40; N, 13.39. $C_{17}H_{13}N_3O_4$ requires: C, 63.15; H, 4.05; N, 13.00%).

(g) 6-{3-[4-(4-Chlorobenzyl)-1-piperazinyl]propyloxy}-N-(4-methoxybenzyl)-9-oxo-9H-benzopyrano[2,3-d]-v-triazole A mixture fo the above 4-methoxybenzyl isomers (0.647 g, 0.002 m) and 1-(4-chlorobenzyl)-4-(3-hydroxypropyl)piperazine (0.537 g, 0.002 m) in dry THF (30 ml) was treated with triphenylphosphine (1.0 g, 0.0038 M) and stirred for a few minutes at room temperature. A solution of diethyl azodicarboxylate (0.90 g, 0.005 M) in THF (5 Ml) was added dropwise and the solution stirred at room temperature for 2 hours. The solvent was evaporated in vacuo and a small volume of ethanol added to the residue, the mixture was heated to reflux and cooled. The white solid which separated was filtered off and washed with ethanol. Drying in vacuo gave 0.347 g, 30%) of the pure N-1 isomer, mp 151°-2° C., $v_{max}$ (mull), 1620, 1660 cm$^{-1}$, δ(CDCl$_3$) 2.0 (2H, m), 2.52 (8H, m), 2.52 (2H, m), 3.47 (2H, s), 3.78 (3H, s), 4.16 (2H, t, J 6 Hz), 5.92 (2H, s), 6.98 (2H, m), 7.02 (4H, ABq, Δv51 Hz, J 9 Hz); 7.32 (4H, s); 8.23 (1H, d, J 10 Hz). (Found: C, 64.69; H, 5.91, N, 12.10; $C_{31}H_{32}ClN_5O_4$ requires C, 64.85; H, 5.62; N, 12.20%).

Evaporation of the ethanol filtrate above and chromatography on silica gel, eluting with chloroform separated the N-2 material. The pure N-2 isomer could be obtained by recrystallisation from ethanol, mp 130°-1° C., $v_{max}$ (mull) 1620, 1660 cm$^{-1}$, δ(CDCl$_3$), 2.00 (2H, m); 2.48 (8H, s), 3.47 (2H, s); 3.78 (3H, s); 4.13 (2H, t, J 6 Hz), 5.61 (2H, s); 6.92 (2H, m); 7.14 (4H, ABq, Δv34 Hz, J 9 Hz), 7.26 (4H, s); 8.26 (1H, d, J 9 Hz).

(h) 6-{3-[4-(4-Chlorobenzyl)-1-piperazinyl]propyoxy}-9-oxo-1H,9H-benzopyrano[2,3-d]-v-triazole

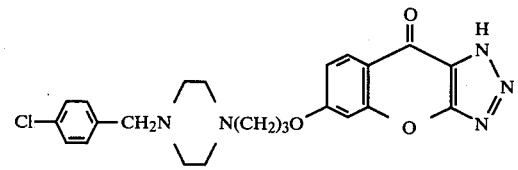

A solution of the mixed 4-methoxybenzyl isomers of the title compound, (0.550 g) in trifluoroacetic acid (10 ml) was stirred at 65° C. for 5 hours and then cooled. After removal of the trifluoroacetic acid in vacuo, water was added and the pH brought to 9 with aqueous sodium hydroxide. After reacidification with glacial acetic acid, the mixture was maintained at 0° C. for 2 days and the pink solid filtered off, washed with water and dried to give 0.470 g of crude solid. Chromatography on silica gel, eluting with chloroform to chloroform/ethanol (1:) gave a white foam which on boiling in ethanol crystallised to give 60 mg (26%) of white solid, mp 215°-16° C. (dec), $v_{max}$ (mull) 1620, 1643 cm$^{-1}$, δ(DMSO d6), 2.03 (2H, m); 2.75 (10H, m); 3.75 (2H, s); 4.19 (2H, t J 6 Hz); 6.98 (1H, dd, J 9 & 2.5 Hz); 7.20 (1H, d, J 2.5 Hz); 7.37 (4H, s); 8.09 (1H, d, J 9 Hz). (Found: C, 60.53; H, 4.83; N, 15.13; Cl, ; $C_{23}H_{24}ClN_5O_3$ requires: C, 60.85; H, 5.33; N, 15.43; Cl 7.82%).

PHARMACOLOGICAL DATA SECTION

ACTIVITIES IN BIOLOGICAL TEST SYSTEMS

The compounds were tested for their ability to:
(a) inhibit rat passive peritoneal anaphylaxis; and
(b) antagonise the spasmogenic effects of histamine or isolated guinea pig ileum.

The methods used are described below.

(a) Rat passive peritoneal anaphylaxis (PPA)

The method has been described previously (Ross, Janet W., Smith, H. and Spicer, Barbara A. Increased vascular permeability during passive peritoneal anaphylaxis in the rat. Int. Arch. Allergy appl. Immun. 51, 226, 1976.)

Animals

Charles River Sprague Dawley male rats of 225-275 g and Dunkin Hartley male white guinea pigs of 250-300 g were used.

Antiserum

Charles River Sprague Dawley male rats of 225 to 275 g were given subcutaneous injections of 10 mg of ovalbumin (chicken egg elbumin; crystallised and lyophilised, grade 3, Sigma London), in 0.5 ml of a suspension prepared by adding 1 ml of a 0.1 mg/ml solution of ovalbumin, in isotonic saline, to 4 ml of a 1% suspension of aluminium hydroxide in saline, (Alhydrogel; Miles Laboratories, England; diluted 1:1 with isotonic saline). The rats were bled by cardiac puncture, under Halothane anaesthesia, on day 10, the blood was pooled and the serum separated, stored at −20° and thawed only once before use. The serum produced 72 L PCA activity in recipient rats to a dilution of 1:64 to 1:32 which was decreased to a dilution of less than 1:2 by heating at 56° for 4 hours.

Passive Peritoneal Anaphylaxis

Rats were given intraperitoneal injections of 2 ml of a 1:5 dilution of the rat anti-serum in isotonic saline. Two hours later 0.3 ml of a 5% solution of Pontamine Sky Blue (Raymond A. Lamb, London) in isotonic saline was injected intraveneously, followed by an intraperitoneal injection of the test compound in 1 ml of saline; (control rats received 1 ml of saline); followed 30 seconds later by an intraperitoneal injection of 5 ml of a Tyrode solution containing 50 µg/ml heparin and 0.4 mg/ml of ovalbumin. The concentrations of the compounds were quoted as those in the 6 ml of fluid injected intraperitoneally. Exactly 5 minutes after challenge the rats were stunned and bled and their peritoneal fluids were collected by opening their peritoneal cavities over funnels into polycarbonate tubes in ice. The supernatants were separated from the cellular residue by centrifuging at 150 g for 5 minutes and any samples obviously contaminated with blood were discarded for estimation of dye, histamine and SRS-A. Groups of at least 5 rats were used for each dose of compound and the treatments were randomized.

Assay of Peritoneal Fluids

Collected peritoneal fluids were immediately cooled to 0° C. and centrifuged and the supernatant fluids assayed for dye within 2 hours. 0.5 ml samples of the supernatants were added to 1 ml of 12% trichloracetic acid and stored at −20° C. and used to assay for histamine. The remainders of the supernatant fluids were placed in a boiling water bath for 5 minutes and stored frozen at −20° C. until assayed for SRS-A.

Dye Assay

The optical densities (OD) at 625 nm of the supernatants were determined. Samples were taken from supernatants with an OD greater than 2 and diluted in Tyrode's solution before reading.

Histamine Assay

Histamine was assayed using an automated spectrofluorimetric system (Technicon Autoanalyser) by a method similar to that of Evans, D. P., Lewis, J. A. and Thomson, D. S.: (An automated fluorimetric assay for the rapid determination of histamine in biological fluids. Life Sci. 12,327, 1973). At the concentration used the compounds tested did not interfere with the assay.

SRS-A Assay

SRS-A was assayed on the isolated guinea pig ileum preparation in the presence of atropine ($5 \times 10^{-7}$ M) and mepyramine maleate ($10^{-6}$ M), the latter to abolish the histamine response. (Brocklehurst, W. E. The release of histamine and formulation of a slow reacting substance (SRS-A) during anaphylactic shock. J. Physiol., Lond. 151, 416, 1960). Bulked peritoneal fluids from passively sensitised and challenged rats were centrifuged, heated, stored at −20° C. in 0.5 ml aliquots, and used as a reference SRS-A standard, and arbitrarily designated as containing 10 Units per ml. Concentrations of the unknown were bracketed by reference SRS-A samples. At the concentrations used, the compounds tested did not interfere with the assay.

(b) Anti-histamine Activity

The anti-histamine activity of these compounds was measured in terms of $pA_2$ values on guinea pig ileum using the method described by Arunlakshana O. and Schild H. O. (Brit J. Pharm., 14, 1959, 48).

The $pA_2$ is defined as the negative logarithm of the molar concentration of antagonist that will reduce the response of a double dose of agonist to that of a single dose.

Method

Assays were carried out using strips of terminal guinea pig ileum suspended in a 4 ml. capacity organ bath. The ileum was immersed in aerated Tyrode solution at a temperature of 30° C. and a tension of 1 gm. was applied to the gut. Longitudinal contractions of the gut were recorded isotonically using a 2LD01 Devices transducer, a R2502-2 Devices optical wedge and a RE511.20 Smiths servoscribe flat bed recorder.

The tissue was constantly immersed in Tyrode solution washing was by fluid displacement from below. Steady responses of the gut to histamine were obtained by adding histamine solutions in a volume of 0.1–0.2 ml to the bath.

Dose response curves were established for histamine using either a $3 \times 3$ or $4 \times 4$ Latin square design for the administration of the histamine doses.

The antagonists were then added to the Tyrode solution to give final concentrations ranging from 5 ng/ml to 640 ng/ml. The dose response curve to histamine were re-established in the presence of increasing doses of the antagonists.

Calculation of the $pA_2$ values

The height of the response was measured in mms and a mean value calculated. Parallel log dose/response curves were plotted on semi-log graph paper for histamine in the absence and presence of the antagonists. The dose of histamine which produced a response of 100 mms were obtained for each curve from the graph and the ratio designated CR was calculated from $$\frac{\text{dose of histamine to give response 100 mms in presence of antagonist}}{\text{dose of histamine to give response 100 mms in absence of antagonist}}$$

A further graph of log CR-1 against the negative log of the molar concentration of the antagonist in the Tyrode solution was then plotted. The $pA_2$ value was obtained where the line bisected the x-axis.

Results

The results obtained in these tests, which are shown in the following Table, demonstrate the ability of the compounds not only to inhibit the release of mediator substances but also to antagonize the effects of released histamine.

TABLE

Compound 1

Concentration in peritoneal

TABLE-continued

| Conc" injected i.p. (M) | fluid as % of mean of controls. (Mean ± SEM, 5-7 rats per group.) | | |
|---|---|---|---|
| | Histamine | SRS—A | Dye |
| $2 \times 10^{-5}$ | $8 \pm 1$ | | $25 \pm 5$ |
| $2 \times 10^{-6}$ | $73 \pm 8$ | | $87 \pm 17$ |
| $2 \times 10^{-7}$ | $100 \pm 10$ | | $87 \pm 5$ |

| Antihistamine Activity (in vitro) | | | | |
|---|---|---|---|---|
| Compound No | pA$_2$ Values obtained in different assays | | | |
| 1 | 9.4 | 9.3 | 9.7 | 9.1 |
| 2 | 7.8 | 7.7 | 7.4 | 7.4 |
| 3 | 8.5 | 8.7 | 8.3 | 8.4 |
| 4 | 7.9 | 8.0 | 8.0 | 8.0 |
| 5 | 8.1 | 7.6 | | |

Toxicity

No toxic effects were observed in these tests.

We claim:

1. A compound of formula (I)

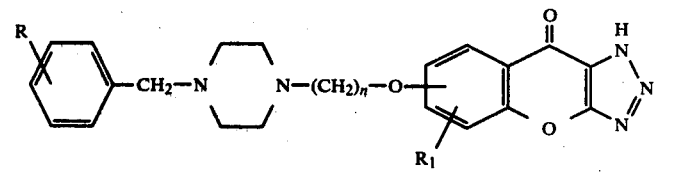

wherein X is phenyl, optionally substituted by one halogen, $C_{1-4}$ alkyl, or $C_{1-4}$ alkoxy; or pyridyl; $R_1$ is hydrogen or $C_{1-6}$ alkyl; and n is 1 to 6; or a pharmaceutically acceptable salt thereof formed with the acidic hydrogen atom of the triazole moiety or with the amino moieties.

2. A compound according to claim 1 of formula (I)':

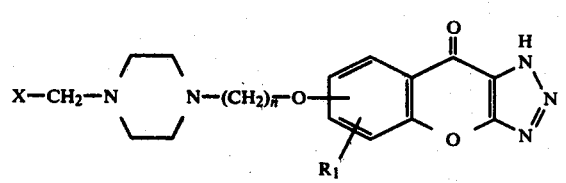

wherein R is hydrogen, halogen, $C_{1-4}$ alkyl or $C_{1-4}$ alkoxy; $R_1$ is hydrogen or $C_{1-6}$ alkyl; and n is 1 to 6 or a pharmaceutically acceptable salt thereof.

3. A compound according to claim 2 which is 6-{3-[4-(4-Methylbenzyl)-1-piperazinyl]propyloxy}-5-methyl-9-oxo-1H,9H-benzopyrano[2,3-d]-v-triazole or 6-{3-[4-(4-Methoxybenzyl)-1-piperazinyl]propyloxy}-5-methyl-9-oxo-1H,9H-benzopyrano[2,3-d]-v-triazole or said pharmaceutically acceptable salt thereof.

4. A compound according to claim 2 of formula (II):

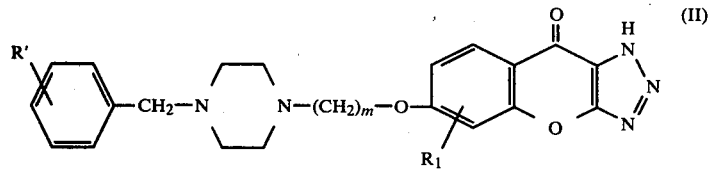

wherein R' is hydrogen or halogen, $R_1$ is hydrogen or $C_{1-6}$ alkyl, and m is 2, 3 or 4 or said pharmaceutically acceptable salt thereof.

5. A compound according to claim 4 which is 6-{3-[4-(4-Chlorobenzyl)-1-piperazinyl]propyloxy}-5-methyl-9-oxo-1H,9H, benzopyrano[2,3-d]-v-triazole or 6-{3-[4-(2-Chlorobenzyl)-1-piperazinyl]propyoxy}-5-methyl-9-oxo-1H, 9H-benzopyrano[2,3-d]-v-triazole or 6-{3-[4-(4-Chlorobenzyl)-1-piperazinyl]propoxy}-9-oxo-1H,9H, benzopyrano[2,3-d]-v-triazole or said pharmaceutically acceptable salt.

6. A compound according to claim 1 of formula (I)":

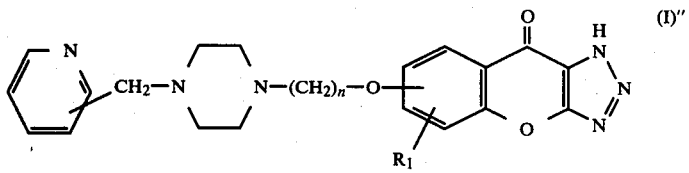

wherein $R_1$ is hydrogen or $C_{1-6}$ alkyl; and n is 1 to 6 or said pharmaceutically acceptable salt thereof.

7. A compound according to claim 6 which is 6-{3-[4-(2-Pyridylmethyl)-1-piperazinyl]propyloxy}-5-methyl-9-oxo-1H,9H-benzopyran-[2,3-d]-v-triazole or said pharmaceutically acceptable salt thereof.

8. A pharmaceutical composition for the prophylaxis or treatment of diseases due to a histamine mediated allergic response in mammals, comprising a therapeutically effective amount of a compound according to claim 1 or said pharmaceutically acceptable salt thereof, and a pharmaceutically acceptable carrier.

9. A method of prophylaxis or treatment of diseases due to a histamine-mediated allergic response in mammals, which method comprises the administration to the sufferer of a therapeutically effective dose of a compound according to claim 1 or said pharmaceutically acceptable salt thereof.

* * * * *